United States Patent [19]

Mullen

[11] Patent Number: 5,231,028
[45] Date of Patent: Jul. 27, 1993

[54] IMMOBILIZED ENZYME ELECTRODES

[75] Inventor: William H. Mullen, Ely, Great Britain

[73] Assignee: Cambridge Life Sciences plc, Cambridge, Great Britain

[21] Appl. No.: 372,339

[22] PCT Filed: Oct. 19, 1988

[86] PCT No.: PCT/GB88/00868
§ 371 Date: Jul. 5, 1989
§ 102(e) Date: Jul. 5, 1989

[87] PCT Pub. No.: WO89/03871
PCT Pub. Date: May 5, 1989

[30] Foreign Application Priority Data

Oct. 19, 1987 [GB] United Kingdom ........... 8724446

[51] Int. Cl.$^5$ .................... C12M 1/40; C12M 1/34
[52] U.S. Cl. ..................... 435/288; 435/291; 435/817; 204/403
[58] Field of Search .......... 435/14, 25, 174, 288, 435/291, 817; 204/1 T, 403, 153.12, 415

[56] References Cited

U.S. PATENT DOCUMENTS

| | | | |
|---|---|---|---|
| 4,044,193 | 8/1977 | Petrow et al. | 429/40 |
| 4,166,143 | 8/1979 | Petrow et al. | 427/115 |
| 4,229,490 | 10/1980 | Frank et al. | 427/113 |
| 4,293,396 | 10/1981 | Allen et al. | 204/106 |
| 4,392,933 | 7/1983 | Nakamura et al. | 204/403 |
| 4,478,696 | 10/1984 | Allen | 204/105 |
| 4,820,399 | 4/1989 | Senda et al. | 204/403 |
| 4,970,145 | 11/1990 | Bennetto | 435/14 |

FOREIGN PATENT DOCUMENTS

| | | |
|---|---|---|
| 0026995 | 4/1981 | European Pat. Off. |
| 0247850 | 2/1987 | European Pat. Off. |
| 55-124060 | 3/1979 | Japan. |
| 56-163447 | 12/1981 | Japan. |
| 8807192 | 9/1988 | PCT Int'l Appl. |
| 1357494 | 6/1974 | United Kingdom. |
| 2191003 | 12/1987 | United Kingdom. |

OTHER PUBLICATIONS

Castner, J. F. and Wingard, L. B., Anal. Chem. 56: 2891-2896 (1984).
Proctor, A., et al., Anal. Chem. 57: 1644-1649 (1985).

Primary Examiner—Michael G. Wityshyn
Assistant Examiner—William H. Beisner
Attorney, Agent, or Firm—St. Onge Steward Johnston & Reens

[57] ABSTRACT

Enzyme electrodes are described which are of reduced sensitivity to alcohol. The electrodes comprise a porous resin-bonded layer of powdered carbon or graphite, onto which the enzyme is immobilized, that layer containing either finely divided platinum oxide, or finely divided platinum the surface of which is provided with a thin oxide film, e.g. by an anodisation process, the finely divided platinum oxide or anodised platinum being uniformly dispersed throughout the resin-bonded carbon or graphite layer and preferably preadsorbed onto the surface of the powdered carbon or graphite prior to bonding. Also disclosed is a method of making such electrodes by a polarization treatment of a preassembled platinized electrode.

20 Claims, No Drawings

IMMOBILIZED ENZYME ELECTRODES

RELATED APPLICATION DATA

This invention relates to an improvement or modification in enzyme electrodes of the type disclosed in previous U.S. application Ser. No. 146,278 to Bennetto, et al., which issued as U.S. Pat. No. 4,970,145.

BACKGROUND OF THE INVENTION

This invention relates, as indicated, to enzyme electrodes, that is to say electrodes carrying an enzyme immobilized thereon and amperometrically responsive to the activity of that enzyme when the electrode is in contact with a sample, e.g., a clinical sample, containing the enzyme substrate.

In U.S. Pat. No. 4,970,145 enzyme electrodes of improved sensitivity and rapid response time are disclosed and which comprise an enzyme layer immobilised onto an electrically conductive carbon substrate, more particularly an electrically conductive carbon substrate having a heterogeneous porous surface layer onto which the enzyme is immobilised and which consists essentially of finely divided particles of a platinum group metal, e.g. platinum or palladium, uniformly dispersed throughout a porous matrix of resin bonded carbon or graphite particles. Preferred resin binders are hydrophobic resin binders, particularly fluorocarbon resins, especially polytetrafluoroethylene.

The heterogeneous, porous surface layer is preferably formed as a resin bonded surface layer on an underlying electrically conductive support, e.g. a metal sheet, or more preferably, a sheet of electrically conductive carbon paper. Alternatively, the porous surface layer may be formed as a resin bonded surface layer on a filamentous web of electrically conductive fibres, e.g. a filamentous web of carbon fibres.

Alternatively, the heterogeneous, porous surface layer may be an integral, self-supporting layer of resin bonded carbon or graphite particles, having said finely divided platinum group metal substantially uniformly dispersed therethrough.

Whilst the resin bonded carbon or graphite particle layer containing the finely divided platinum group metal can be formed by suitably moulding a uniform mixture containing said carbon or graphite particles and said finely divided platinum group metal, the finely divided platinum group metal is preferably preadsorbed onto the surface of the carbon or graphite particles, prior to the moulding thereof to form said resin bonded layer. Materials made according to that technique, which is disclosed in detail in GB-A-1,357,494, and U.S. Pat. Nos. 4,044,193 and 4,166,143, or in U.S. Pat. Nos. 4,229,490 and 4,293,396 for supported versions thereof, are in fact commercially available materials heretofore used as gas diffusion electrodes in fuel cells, and available from the Prototech Company of Newton Highlands, Mass., United States of America.

Whilst the novel enzyme electrodes described above and disclosed in more detail in the previous application are highly advantageous in giving extremely rapid response times, high output current densities, remarkable storage stability when wet, and require relatively low operating potentials, giving rise to low background noise, it has been found that such enzyme electrodes are alcohol sensitive, that is to say, they give rise to false readings, and a general increase of background current, in the presence of alcohol, especially ethanol, and thus cannot be used for the reliable determination of analytes, e.g. glucose, in samples containing quantities of alcohol (ethanol).

SUMMARY OF THE INVENTION

Accordingly an object of this invention is to provide an enzyme electrode of the kind described in U.S. Pat. No. 4,970,145, but which has reduced alcohol sensitivity and which may therefore be used at a fixed potential in the amperometric measurement of substrate concentrations in a sample, particularly clinical samples, containing amounts of alcohol.

A further object is to provide a method of treating enzyme electrodes of the type described in U.S. Pat. No. 4,970,145 to reduce their alcohol sensitivity.

In accordance with a first aspect of the present invention, it has been found that such alcohol sensitivity can be controlled by using as the finely divided platinum group metal finely divided platinum which has been subjected to a controlled oxidation treatment, thereby to form a thin oxide film on the surface of the metal particles. Whilst this can be done prior to formation of the electrode substrate, i.e. before moulding the platinished carbon or graphite particles, or the powdered mixture of finely divided platinum metal and carbon or graphite, the surface oxidation can be more easily achieved by anodising the metal particles in situ, for example by subjecting the electrode material to a polarisation treatment, which may be carried out before or after immobilisation of the enzyme, preferably before.

In a second aspect, it has been found that, in enzyme electrodes of the foregoing type, the platinum group metal can be substituted, in whole or in part, by platinum oxide. As previously, the electrically conductive support for the immobilised enzyme may be formed by moulding a preformed mixture of powdered carbon or graphite, powdered platinum oxide, with or without additional finely divided platinum group metal, and a resin binder, preferably a hydrophobic resin binder, e.g. a fluorocarbon resin such as polytetrafluoroethylene, into either a self-supporting porous layer of resin-bonded carbon or graphite particles having said platinum oxide, and said platinum metal if present, substantially uniformly dispersed throughout said layer, or more preferably, as a porous surface layer on an underlying, preferably electrically conductive support, e.g. of metal, electrically conductive carbon paper or a carbon fibre fabric. More preferably, however, the platinum oxide, with or without additional platinum metal, is adsorbed onto the surface of the carbon or graphite powder particles prior to bonding with said resin. Alternatively, in accordance with the first aspect of the present invention, there may be used finely divided platinum metal, the particle surface of which is oxidised under controlled conditions to form a thin oxide film thereon, either before or after the adsorption thereof onto the carbon or graphite particles.

DETAILED DESCRIPTION OF THE INVENTION

The enzyme electrodes of this invention comprise an electrically conductive substrate of resin bonded carbon or graphite particles and onto which substrate the enzyme is immobilized, that substrate further containing as a uniform dispersion therein a material selected from the group consisting of a) finely divided particles of platinum oxide and b) finely divided particles of elemental platinum metal, the surface of which has been oxidized, e.g., by anodization.

As the carbon graphite powder there may be used any suitable carbon or graphite powder which readily permits the subsequent immobilisation of the enzyme, and to this end, carbon powders should be used having a high density of functional groups, such as carboxylate, amino and sulphur-containing groups, on the surface, as opposed to the more vitreous and glassy carbons, which bind enzymes only poorly. Particle size may range from 3 to 50 nm, more usually 5 to 30 nm.

Platinum oxide, which term is hereinafter used to embrace oxidised, e.g. anodised, particles of platinum, may be deposited onto the carbon particles in any convenient fashion, e.g. by adsorption onto the carbon and graphite particles from suspension in a suitable liquid vehicle, to give platinum oxide loadings of from 0.1 to 20% by weight, based on the weight of carbon, preferably from 0.5 to 5%. These limits are, however, practical rather than critical. Below about 0.1% platinum oxide the output signal falls to a level which, in practical terms, is too low to be measured except by very sensitive apparatus. Above about 20%, the loading of platinum oxide becomes uneconomic, with little additional benefit in terms of response time, sensitivity etc. Indeed with extremely high metal loadings the sensitivity begins to fall.

Following deposition or adsorption of the platinum oxide onto the carbon or graphite particles the powder is moulded using a suitable resin binder, preferably a fluorocarbon resin such as polytetrafluoroethylene to form either a completely self-supporting porous moulded structure consisting essentially of said resin bonded, oxide containing carbon powder particles, or more usually a porous moulded surface layer of such resin-bonded particles bonded to an electrically conductive substrate, e.g. of metal, carbon or graphite. A particularly preferred substrate material for the moulded resin-bonded platinised carbon layer is carbon paper as taught by U.S. Pat. No. 4,229,490 or an open pore carbon cloth as taught by U.S. Pat. No. 4,293,396. In order to retain maximum porosity the amount of resin used as the binding agent should be the minimum required to provide mechanical integrity and stability to the electrode layer, such layer usually having a thickness no more than about 0.1 to 0.5 mm, although greater thicknesses may be employed. Subject to the requirements of structural integrity, mechanical strength, and porosity, amounts of binding resin are not critical and may range from as little as 5 or 10% by weight, based on the amount of oxide containing carbon powder, up to as much as 80%, but with the amount more usually in the range 30 to 70% by weight. A variety of resins may be used, including resins which are conducting or semi-conducting, but preferred are synthetic fluorocarbon resins, particularly polytetrafluoroethylene. In view of the small but essential requirement for oxygen in the oxidation process it is essential that the binder be permeable to oxygen. To this end the binder should have a minimum solubility towards oxygen at atmospheric pressure of at least $2 \times 10^{-3}$ cm$^3$ O$_2$ (measured at standard temperature and pressure) per cm$^3$ of polymer.

Suitable binders and their known oxygen solubilities taken from The Polymer Handbook (Ed. J. Brandrup and E. H. Immergut) 1st Ed. (1967), Interscience, include:

|  | $S \times 10^2$ (cm$^3$) |
|---|---|
| Polytetrafluoroethylene (PTFE) | 0.276 |
| Fluorocarbon polymers other than PTFE | Variable, 0.2 upwards |
| Polyethylmethacrylate | 8.6 |
| Polystyrene | 18.2 (calculated) |
| Polyvinyl acetate | 6.3 |
| Polyvinyl chloride | 2.92 |
| Polycarbonate | 0.51 |
| Poly(4-methylpentene-1) | 24.3 |
| Polyisoprene | 10.3 |
| Polychloroprene | 7.5 |
| Poly 1,3-butadiene | 9.7 |
| Silicone rubber | 31.1 |

The preferred enzyme electrode substrates used in accordance with this invention are, in fact, similar to those platinised carbon electrode materials sold by the Prototech Company of Newton Highlands, Mass., and used heretofore as electro-catalytic gas diffusion electrodes in fuel cells, but wherein the platinum component is replaced by platinum oxide, or in which the platinum component is anodised prior to adsorption onto the carbon powder. The preparation of such materials is similar to that described in detail in U.S. Pat. Nos. 4,044,193, 4,166,143, 4,293,396 and 4,478,696, to which reference should be made for full details, except that finely divided platinum oxide is used in place of the finely divided platinum, or else the finely divided platinum is given a surface oxidation, e.g. polarisation treatment, before or after adsorption of the platinum onto the carbon or graphite, and/or before or after moulding with said resin. In broad detail, however, colloidal platinum or platinum oxide with a particle size in the range 15 to 25 Angstroms (1.5 to 2.5 nm) is adsorbed onto the surface of powdered carbon (particle size 50 to 300 Angstroms: 5 to 30 nm), for example, by formation of a platinum sol in situ in the presence of powdered carbon which acts as a nucleating agent for the sol. The platinised carbon particles are then moulded onto an electrically conductive supporting structure, e.g. a sheet of carbon paper, using a synthetic resin binder, preferably a fluorinated hydrocarbon resin, and especially polytetrafluoroethylene, followed, in the case of finely divided platinum, with a surface oxidation, e.g. polarisation treatment to provide an oxidised surface on the platinum particles.

In an alternative, the platinum or platinum oxide containing carbon particles may be impregnated into a preformed porous carbon cloth and bonded therein using the resin binder, preferably polytetrafluoroethylene, again before or after surface oxidation of the finely divided platinum. In another alternative, there may be used carbon paper electrodes of the type comprising a carbon paper support member, preferably impregnated with a water-repellent resin such as polytetrafluoroethylene, and onto which is deposited, e.g. by screen printing, a resin bonded catalyst layer comprising either a uniform mixture of platinum oxide and carbon or graphite particles, bonded with a resin binder, preferably again polytetrafluoroethylene, or a uniform mixture of finely divided platinum and carbon or graphite, the finely divided platinum having or being subsequently provided with a surface oxide film.

The immobilisation of the enzyme on the surface of the resin-bonded, carbon substrate can be carried out using a variety of well established immobilisation techniques, for example, covalent bonding with a carbodiimide or a carbonyldiimidazole reagent, covalent bonding with 1,6-dinitro-3,4-difluorobenzene (DFDNB), or cross-linking with glutaraldehyde.

Typical exemplary protocols for the immobilization of the enzyme, glucose oxidase, are as follows:

A. Carbodiimide Treatment:
1. Cut out pieces of electrode of suitable size from the sheet of electrode material.
2. Immerse the electrodes in ethanol for about 5 minutes to ensure thorough wetting of the PTFE coated binder and backing.
3. Remove the electrodes from the ethanol and wash them thoroughly with distilled water to remove all traces of ethanol.
4. Prepare 5 ml (or less) of a 0.15M solution of 1-cyclohexyl-3-(2-morpholino)carbodiimide p-methyltoluene sulphonate in 0.1M pH 4.5 acetate buffer and place the electrodes in this for 90 minutes at room temperature. Gentle agitation with a mechanical shaker may be used. Should the electrodes float on the surface of the solution then they have not been sufficiently wetted, and the treatment should be repeated from step 2.
5. Remove the electrodes and wash them thoroughly with distilled water. Place them in a freshly prepared solution of glucose oxidase (5.0 mg/ml) in pH 5.6 acetate buffer for 90 minutes at room temperature with gentle mechanical shaking.
6. Remove the electrodes from the enzyme solution and rinse them thoroughly with 0.1M acetate buffer. The electrodes are now ready for use.
7. Store the electrodes at 4° C. in 0.1M pH 5.6 acetate buffer.

B. Carbonyldiimidazole Treatment:
1. Carry out step 1 above and omit steps 2 and 3.
2. Prepare a solution of N,N'-carbonyldiimidazole in anhydrous dimethyl formamide (40 mg/ml).
3. Place the electrodes in this solution for 90 minutes at room temperature with gentle mechanical shaking if desired.
4. Remove the electrodes from the solution and dry off the excess carbonyldiimidazole solution before placing them in a freshly prepared solution of glucose oxidase for a further 90 minutes.
5. Carry out steps 6 and 7 above.

C. DFDNB Treatment:
1. Carry out steps 1-3 under A above.
2. Wash the electrodes thoroughly in sodium borate buffer (0.1M, pH 8.5).
3. Prepare a solution of 1,6-dinitro-3,4-difluorobenzene in methanol (0.1021 g/5 ml) and place the electrodes in this for 10 minutes at room temperature.
4. Remove the electrodes and wash them thoroughly with borate buffer before placing them in a solution of glucose oxidase for a further 90 minutes at room temperature.
5. Carry out steps 6 and 7 under A above.

Other types of coupling agent may be used for the immobilisation process, including bifunctional agents of variable chain length, for example diimidates such as dimethylmalonimidate or dimethylsuberimidate.

In the alternative, it has been found that simple adsorption of the enzyme onto the platinum oxide containing resin-bonded carbon powder support, i.e. without cross-linking, is effective with some enzymes, and in particular with glucose oxidase.

Usually, but not necessarily, the surface layer of immobilised enzyme will be physically protected by the application of a suitably porous, e.g. polycarbonate, film or membrane which must, of course, be permeable by the enzyme substrate (glucose) which is to be determined. Such membranes are somewhat disadvantageous in increasing the response time of the sensor, but nevertheless even with such a membrane the present sensors are capable of response times comparable with, and in many cases, substantially better than, conventional enzyme electrodes.

As already indicated, the invention relates particularly to glucose oxidase electrodes, i.e. in which the immobilised enzyme is a glucose oxidase, but it will be apparent that other oxidoreductases can be used, although not always with equivalent effect. This is not necessarily due to any inherent ineffectiveness of the enzyme, but to other factors. For example, in the determination of oxalic acid using oxalate oxidase the oxalic acid substrate itself undergoes electrochemical oxidation at the base electrode, thus largely masking any effect from the enzyme. However, other suitable oxidoreductases include lactate oxidase, galactose oxidase, cholesterol oxidase and other peroxide producing enzymes as well as combinations of immobilised enzymes, including combinations of a non-oxidase and an oxidase, the first acting on a substrate of interest to produce an oxidisable substrate for the oxidase, the latter acting on the oxidisable product to produce a measurable current which is proportional to the concentration of the substrate of interest. One such combination is the combination of beta-galactosidase and glucose oxidase (for the quantitative determination of lactose), or the combination of a beta-glucan depolymerising enzyme, beta-glucosidase and glucose oxidase (for the determination of beta-glucans).

Other types of sensor application include the use of enzymic or non-enzymic reagents or processes which interact with a primary substrate of interest in a precursor reaction, the resulting product including a substance which in turn acts as a substrate for an enzyme electrode according to this invention. Many examples of such precursor steps will be found in the field of immunochemical reactions, and methods of using such reactions in the construction of sensors, including immunosensors, utilizing enzyme electrodes according to the present invention will be apparent to those skilled in the art.

However, the primary application of the electrodes according to the invention will be as biosensors for the detection and/or quantitative measurement of an oxidisable substrate, especially glucose, in a sample, especially a clinical sample such as blood, serum, plasma, urine, sweat, tears and saliva. It is in such applications that the relative insensitivity of the present oxide containing electrode to ethanol is particularly advantageous.

Other possible, non-clinical applications include:
(a) fermentation monitoring,
(b) industrial process control,
(c) environmental monitoring, e.g. effluent and pollution control of liquids and gases,
(d) food testing,
(e) veterinary applications, particularly applications allied to the clinical applications suggested above.

In so far as bio- and other sensors incorporating an enzyme electrode material according to the present invention may comprise other structural elements, electrical leads, electrically non-conductive (insulating) supports or probes, etc., such elements in the construction are conventional and need not be described in detail. Suffice it to say that, where, as will usually be the case, the electrode material is a paper thin sheet or wafer, the biosensor will usually include an insulating support member or probe upon which the electrode material is mounted and by means of which the electrode material can be introduced into the sample. In such cases the actual size of the piece of electrode material may be quite small, no more than a few square millimeters, or even smaller. Electrical contact with the electrode material may be made in many ways, for example, by mounting the electrode material in face to face contact with an electrically conductive contact or terminal, e.g. of platinum, silver or other suitable conductor. Where the electrode material is of sufficient thickness and strength to be completely self-supporting, insulating supports or carriers for the electrode material can be dispensed with, and electrical leads connected directly to the surface of the electrode material.

In the alternative method of this invention, i.e. in situ oxidisation of the finely divided platinum metal, in enzyme electrodes of the type disclosed in U.S. Pat. No. 4,970,145, this may be achieved by exposing the electrically conductive substrate, before or after immobilisation of the enzyme to a polarisation treatment effective to anodise the surface of the platinum particles present in the electrode. Such a treatment may be effected by polarising the electrode substrate to a positive potential, with reference to a silver/silver chloride electrode, for a short period of time, e.g. from 1 to 30 minutes. The actual value of the applied potential is not critical, although below about +1000 mV, treatment times may become excessive. Similarly the maximum is governed by practical considerations, since too high a potential will result in too high a current density with possible consequential damage or destruction of the electrode material, to say nothing of inactivation of the enzyme. For all practical purposes polarisation at from +1000 mV to +2000 mV, measured with reference to silver/silver chloride, preferably +1200 mV to +1500 mV has been found to be satisfactory and to give reasonably short treatment times, i.e. from 1 to 30 minutes. In some cases a cyclical polarisation treatment may be used including alternate polarisation cycles at, for example, ±2 volts, preferably +1.5 volts to −1.5 volts with reference to a silver/silver chloride electrode, provided that the cyclical polarisation finishes at a positive potential with reference to silver/silver chloride. Polarisation at a negative potential, or termination at a negative potential with reference to silver/silver chloride may increase ethanol sensitivity.

The reduction in ethanol sensitivity obtained with the above method is illustrated by the following data. For this purpose the current output was measured from 2 mm discs of platinised carbon paper (obtained from The Prototech Company) in the presence of 1% v/v ethanol using a cell of the type shown in FIG. 15 of the drawings of U.S. Pat. No. 4,970,145. For the measurement of the response to ethanol, the electrode material was poised at various different potentials, as indicated, and measurements were made both before and after polarisation:

| Operating potential mV | Output Current (μA) 1% v/v ethanol | |
| --- | --- | --- |
| | Platinised carbon paper (untreated) | Platinised carbon paper after cyclic polarization at +1.0 volts for 10 min −1.5 volts for 10 min +1.5 volts for 30 min |
| 200 | 0.5 | 0.15 |
| 280 | 0.6 | 0.3 |
| 340 | 0.75 | 0.5 |
| 400 | 1.0 | 0.6 |
| 500 | 2.15 | 1.2 |
| 600 | 3.0 | 1.3 |

The following data has been obtained using 2 mm diameter enzyme electrodes of the type disclosed in U.S. Pat. No. 4,970,145 and comprising glucose oxidase immobilised onto platinised carbon paper electrode material obtained from the Prototech Company, using the polarographic cell disclosed in that application, and in which the electrodes were polarised anodically before immobilisation of the enzyme. The same electrodes treated in the same way were also measured for ethanol sensitivity using a 0.2% v/v ethanol solution. Polarisation was effected in a 3-electrode cell at the potentials indicated, such potentials being with reference to a silver/silver chloride electrode:

| Polarisation Treatment | Current μA | |
| --- | --- | --- |
| | 10 mM Glucose | 0.2% v/v ethanol |
| Unpolarised electrode | 6.25 | 1.55 |
| +1200 mV for 10 minutes | 7.0 | 0.25 |
| +1200 mV for 30 minutes | 6.7 | 0.22 |
| +1500 mV for 10 minutes | 6.8 | 0.14 |

Such results shown the substantial (<12 x) reduction in ethanol sensitivity obtained by the polarisation treatment.

To illustrate the use of platinum oxide, a carbon paper electrode similar to those described in U.S. Pat. No. 4,970,145 but containing finely divided platinum oxide predispersed onto the carbon particles prior to bonding onto a carbon paper substrate, in place of platinum, was immersed overnight in a phosphate buffer pH 7 containing 5 mg/mL glucose oxidase. As a result glucose oxidase was adsorbed onto the surface of the platinum oxide containing carbon paper electrode. Glucose and ethanol sensitivities of the enzyme electrode material were determined in the manner previously described using a 2 mm disc of electrode material at an applied potential of 280 mV:

| | 10 mM Glucose | 0.2% v/v ethanol |
| --- | --- | --- |
| Current output (μA) | 7.0 | 0.1 |

These figures again demonstrate the high substrate sensitivity, and low alcohol (ethanol) sensitivity, obtained using platinum oxide containing resin bonded carbon paper enzyme electrodes.

I claim:
1. In an enzyme electrode comprising
   a) an electrically conductive support member comprising a porous, electrically conductive layer of resin-bonded carbon or graphite particles having a particle size in the range of about 3 to about 50 nm and having dispersed throughout said layer and in intimate contact with said carbon or graphite particles, finely-divided particles of or containing a platinum group metal having a particle size in the range of about 15 to 25 Angstroms, said carbon or graphite particles and said platinum group metal or metal-containing particles being bonded to-gether by a synthetic resin into a heterogeneous, porous substrate consisting essentially of resin-bonded carbon or graphite particles having said platinum group metal or metal-containing particles distributed uniformly throughout said layer, and b) an effective amount of an enzyme uniformly distributed throughout said porous layer and in intimate contact with said carbon or graphite particles and said platinum group metal or metal-containing particles, said electrode being amperometrically and directly responsive to the activity of said enzyme when the electrode is immersed at an applied fixed potential in a liquid sample containing a substrate for the enzyme, an improvement which comprises using, as said metal or metal-containing particles, particles selected from the group consisting of i) particles consisting entirely of platinum oxide, and ii) particles of platinum that have been oxidized to provide a surface film of platinum oxide on the surface of the particles.

2. An enzyme electrode according to claim 1, wherein the synthetic resin is a hydrophobic synthetic resin.

3. An enzyme electrode according to claim 1, wherein the synthetic resin is a fluorocarbon resin.

4. An enzyme electrode according to claim 3, wherein the fluorocarbon resin is polytetrafluoroethylene.

5. An enzyme electrode according to claim 1, wherein the particles of platinum oxide or oxidized platinum metal are adsorbed on the surface of the particles of carbon or graphite.

6. An enzyme electrode according to claim 1, wherein said heterogeneous substrate of resin-bonded carbon or graphite particles contains platinum particles, the surface of which has been anodised to provide a thin oxide film thereon.

7. An enzyme electrode according to claim 1, wherein the enzyme is an oxido-reductase.

8. An enzyme electrode according to claim 7, wherein the oxidoreductase is glucose oxidase.

9. An enzyme electrode according to claim 1, wherein said heterogeneous substrate of resin-bonded carbon or graphite particles comprising said platinum oxide, or said oxidised particles of platinum, is provided as a porous surface layer bonded to an underlying support member.

10. An enzyme electrode according to claim 9, wherein said underlying support member is electrically conductive.

11. An enzyme electrode according to claim 10, wherein the electrically conductive support member is an electrically conductive carbon paper.

12. An enzyme electrode according to claim 1, wherein the surface which is exposed to the liquid sample is protected by a microporous membrane permeable to said substrate.

13. An enzyme electrode according to claim 12, wherein said membrane is a polycarbonate membrane.

14. A method of reducing the alcohol sensitivity of an enzyme electrode comprising:

a) an electrically conductive support member comprising a porous, electrically conductive layer of resin-bonded carbon or graphite particles having a particle size of about 3 to about 50 nm, and having dispersed throughout said layer and in intimate contact with said carbon or graphite particles, finely divided particles of platinum said carbon or graphite particles and said platinum particles being bonded together by a synthetic resin into a heterogeneous porous substrate consisting essentially of resin-bonded carbon or graphite particles having said finely-divided platinum particles distributed uniformly throughout the layer, and b) an effective amount of an enzyme uniformly distributed throughout said porous layer, and in intimate contact with said carbon or graphite particles and said finely-divided platinum particles, said electrode being amperometrically and directly responsive to the activity of said enzyme when the electrode is immersed at an applied fixed potential in a liquid sample containing a substrate for the enzyme, which method comprises the step of subjecting the platinum particles to an anodization treatment, before or after incorporation into the electrically conductive layer of resin-bonded carbon or graphite particles, thereby to provide said platinum particles with an anodized surface.

15. A method according to claim 14, wherein said anodization treatment is effected after the incorporation of the platinum particles into the porous layer of resin-bonded carbon or graphite particles and before or after the enzyme is uniformly distributed throughout the porous layer.

16. A method according to claim 15, wherein said anodisation is effected by subjecting the electrically conductive support member comprising said particles incorporated thereon in said porous layer, to a polarisation treatment.

17. A method according to claim 16, wherein said anodisation treatment comprises subjecting the electrically conductive support member comprising said particles, to a polarisation at a potential of from $+1$ to $+2$ volts with reference to a silver/silver chloride electrode for a period of from 1 to 30 minutes.

18. A method according to claim 16, wherein the polarisation treatment is effected at a potential of about $+1.5$ volts with reference to a silver/silver chloride electrode.

19. A method according to claim 16, wherein said polarisation treatment comprises exposing the electrode to cyclical polarisation at potentials of about $\pm 2$ volts with reference to a silver/silver chloride reference electrode for a period of from 1 to 30 minutes.

20. A method according to claim 19, wherein said cyclical polarisation treatment is effected over the range $\pm 1.5$ volts with reference to a silver/silver chloride reference electrode.

* * * * *